United States Patent
Tai et al.

(10) Patent No.: US 11,701,504 B2
(45) Date of Patent: Jul. 18, 2023

(54) IMPLANTABLE INTRACRANIAL PRESSURE SENSOR

(71) Applicants: California Institute of Technology, Pasadena, CA (US); The Regents of the University of California, Oakland, CA (US)

(72) Inventors: Yu-Chong Tai, Pasadena, CA (US); Aubrey M. Shapero, Santa Clara, CA (US); Shane S. Shahrestani, Yorba Linda, CA (US); Azita Emami, Pasadena, CA (US); Abhinav Agarwal, Pasadena, CA (US); Kuang-Ming Shang, Pasadena, CA (US); Sunghoon Kim, San Ramon, CA (US); Olajire Idowu, Lafayette, CA (US); Kurtis I. Auguste, Oakland, CA (US)

(73) Assignees: California Institute of Technology, Pasadena, CA (US); The Regents of the University of California, Oakland, CA (US)

( * ) Notice: Subject to any disclaimer, the term of this patent is extended or adjusted under 35 U.S.C. 154(b) by 121 days.

(21) Appl. No.: 17/150,986

(22) Filed: Jan. 15, 2021

(65) Prior Publication Data

US 2021/0220627 A1   Jul. 22, 2021

Related U.S. Application Data

(60) Provisional application No. 62/962,418, filed on Jan. 17, 2020.

(51) Int. Cl.
  *A61M 27/00*   (2006.01)

(52) U.S. Cl.
  CPC ... *A61M 27/006* (2013.01); *A61M 2205/3344* (2013.01); *A61M 2205/3368* (2013.01);
  (Continued)

(58) Field of Classification Search
  CPC ........ A61M 27/006; A61M 2205/3344; A61M 2205/3368; A61M 2205/3523;
  (Continued)

(56) References Cited

U.S. PATENT DOCUMENTS

| 3,341,794 A | 9/1967 | Stedman |
| 3,838,684 A | 10/1974 | Manuel et al. |

(Continued)

FOREIGN PATENT DOCUMENTS

| CN | 2366109 Y | 3/2000 |
| CN | 101032400 A | 9/2007 |

(Continued)

OTHER PUBLICATIONS

Frank G. Shellock, Jörg Knebel, Angelina D. Prat, Evaluation of MRI issues for a new neurological implant, the Sensor Reservoir, 2013, Magnetic Resonance Imaging, vol. 31, Issue 7, pp. 1245-1250 (Year: 2013).*

(Continued)

*Primary Examiner* — Kai H Weng
*Assistant Examiner* — Brandon W. Levy
(74) *Attorney, Agent, or Firm* — Kilpatrick Townsend & Stockton LLP (57) ABSTRACT

A long-lasting, wireless, biocompatible pressure sensor device is integrated within a hydrocephalus shunt, either within the shunt's reservoir/anchor or as an inline or pigtailed connector. When integrated within a typical reservoir, the device can sit within the reservoir's hollow frustum area covered by the resilient silicone dome of the reservoir. When integrated as an inline connector, the device can sit at any point on the peritoneal catheter or ventricular catheter, including between the VP shut's valve and reservoir. The pressure sensor device includes electronics that can be powered wirelessly by a reader held to a patient's scalp, and (Continued)

so no battery may be required. The reader can transmit an ambient, atmospheric pressure reading from outside the skull to the implanted device so that its electronics can calculate a calibrated gauge pressure internally and then relay it to a patient's smart phone.

20 Claims, 8 Drawing Sheets

(52) U.S. Cl.
CPC . *A61M 2205/3523* (2013.01); *A61M 2205/50* (2013.01); *A61M 2207/00* (2013.01)

(58) Field of Classification Search
CPC .......... A61M 2205/50; A61M 2207/00; A61M 27/00; A61M 27/002; A61M 2202/0464; A61M 2210/0693; A61M 2205/3327; A61M 1/84; A61M 2205/04; A61F 9/00781; A61B 2562/00; A61B 5/00; A61B 5/031; A61B 5/0031; A61B 2562/168; A61B 5/0008; A61B 5/6868; A61B 5/6852

See application file for complete search history.

(56) References Cited

U.S. PATENT DOCUMENTS

| | | | |
|---|---|---|---|
| 4,264,889 A | 4/1981 | Yamamoto et al. | |
| 4,519,401 A | 5/1985 | Leung et al. | |
| 4,586,018 A | 4/1986 | Bettman | |
| 4,604,900 A | 8/1986 | Knudsen et al. | |
| 4,662,226 A | 5/1987 | Wang et al. | |
| 4,846,191 A | 7/1989 | Brockway et al. | |
| 5,067,491 A | 11/1991 | Taylor, II et al. | |
| 5,535,752 A | 7/1996 | Halperin et al. | |
| 6,010,461 A | 1/2000 | Haniff et al. | |
| 6,134,970 A | 10/2000 | Kumakawa et al. | |
| 6,148,673 A | 11/2000 | Brown | |
| 6,221,024 B1 | 4/2001 | Miesel | |
| 6,248,080 B1* | 6/2001 | Miesel | A61B 5/0215 600/311 |
| 6,439,055 B1 | 8/2002 | Maron et al. | |
| 6,733,485 B1* | 5/2004 | Whitehurst | A61M 31/002 604/20 |
| 8,313,811 B2 | 11/2012 | Hogg et al. | |
| 8,313,819 B2 | 11/2012 | Hogg et al. | |
| 8,361,591 B2 | 1/2013 | Hogg et al. | |
| 8,529,538 B2 | 9/2013 | Pang et al. | |
| 8,603,024 B2 | 12/2013 | Bohm et al. | |
| 8,764,685 B2 | 7/2014 | Casey | |
| 8,926,510 B2 | 1/2015 | Marshall et al. | |
| 11,122,975 B2 | 9/2021 | Rodger et al. | |
| 2001/0045509 A1 | 11/2001 | Al-Ali et al. | |
| 2002/0073783 A1 | 6/2002 | Wilner et al. | |
| 2004/0020300 A1 | 2/2004 | Boehler et al. | |
| 2004/0073122 A1 | 4/2004 | Stofer et al. | |
| 2004/0162545 A1 | 8/2004 | Brown et al. | |
| 2004/0176672 A1 | 9/2004 | Silver et al. | |
| 2005/0020962 A1* | 1/2005 | Reich | A61M 27/006 604/8 |
| 2005/0288596 A1 | 12/2005 | Eigler et al. | |
| 2006/0071286 A1 | 4/2006 | Axelrod et al. | |
| 2006/0189887 A1 | 8/2006 | Hassler et al. | |
| 2006/0189917 A1 | 8/2006 | Mayr et al. | |
| 2006/0211914 A1 | 9/2006 | Hassler et al. | |
| 2007/0118038 A1 | 5/2007 | Bodecker et al. | |
| 2007/0243230 A1 | 10/2007 | de Juan, Jr. et al. | |
| 2008/0139959 A1 | 6/2008 | Miethke et al. | |
| 2008/0214983 A1* | 9/2008 | Mauge | A61F 2/2476 604/9 |
| 2010/0030103 A1* | 2/2010 | Lutze | A61B 5/0008 600/561 |
| 2010/0076366 A1* | 3/2010 | Henderson, Sr. | A61B 5/076 604/9 |
| 2010/0312188 A1 | 12/2010 | Robertson et al. | |
| 2011/0066046 A1 | 3/2011 | Young et al. | |
| 2011/0071454 A1 | 3/2011 | Dos Santos et al. | |
| 2011/0071456 A1 | 3/2011 | Rickard | |
| 2011/0071458 A1 | 3/2011 | Rickard | |
| 2011/0071459 A1 | 3/2011 | Rickard et al. | |
| 2011/0132097 A1 | 6/2011 | Hegner et al. | |
| 2011/0160560 A1 | 6/2011 | Stone | |
| 2011/0271764 A1 | 11/2011 | Lee | |
| 2011/0296925 A1 | 12/2011 | Miesel et al. | |
| 2012/0197231 A1 | 8/2012 | Kane et al. | |
| 2012/0247227 A1 | 10/2012 | Crivelli | |
| 2013/0062713 A1 | 3/2013 | Sakuragi et al. | |
| 2013/0137958 A1 | 5/2013 | Tai et al. | |
| 2013/0150776 A1 | 6/2013 | Boehm et al. | |
| 2013/0233086 A1 | 9/2013 | Besling et al. | |
| 2014/0005569 A1* | 1/2014 | Miethke | G01L 19/0046 72/347 |
| 2014/0171777 A1 | 6/2014 | Sanchez et al. | |
| 2014/0276346 A1* | 9/2014 | Sadanand | A61B 5/031 604/9 |
| 2014/0288459 A1* | 9/2014 | Yadav | A61B 5/6852 600/561 |
| 2014/0296687 A1 | 10/2014 | Irazoqui et al. | |
| 2015/0057595 A1 | 2/2015 | Gunn et al. | |
| 2016/0235296 A1 | 8/2016 | Dunning | |
| 2016/0235298 A1 | 8/2016 | Gunn | |
| 2016/0249818 A1 | 9/2016 | Philipp et al. | |
| 2016/0287101 A1* | 10/2016 | Tai | A61B 5/03 |
| 2016/0349162 A1 | 12/2016 | Ebert et al. | |
| 2017/0014270 A1 | 1/2017 | Tyler | |
| 2017/0095163 A1 | 4/2017 | Bitzer et al. | |
| 2019/0307997 A1* | 10/2019 | Auvray | A61B 5/031 |
| 2020/0001058 A1† | 1/2020 | Miethke | |

FOREIGN PATENT DOCUMENTS

| | | |
|---|---|---|
| CN | 200942206 Y | 9/2007 |
| CN | 101918066 A | 12/2010 |
| CN | 102202719 | 9/2011 |
| CN | 203620057 U | 6/2014 |
| CN | 104010568 | 8/2014 |
| CN | 205041352 U | 2/2016 |
| CN | 107529985 | 1/2018 |
| DE | 102004056757 | 6/2006 |
| EP | 1312302 | 5/2003 |
| JP | 2008539811 | 11/2008 |
| JP | 2010503220 | 1/2010 |
| JP | 2013545973 | 12/2013 |
| JP | 2014208301 | 11/2014 |
| WO | 03094693 | 11/2003 |
| WO | 2005022110 | 3/2005 |
| WO | 2008140395 | 11/2008 |
| WO | 2011035262 | 3/2011 |
| WO | 2013003754 A1 | 1/2013 |
| WO | 2014055989 | 4/2014 |
| WO | 2014195372 | 12/2014 |
| WO | 2016160402 | 10/2016 |

OTHER PUBLICATIONS

"Wacker Silicone Fluids AK", Wacker-Chemie GmbH, Available online at: https://www.behlke.com/pdf/wacker_silicone_oil.pdf, Jan. 2002, 12 pages.

Binh-Khiem et al., "Tensile Film Stress of Parylene Deposited Liquid", Langmuir Article, vol. 26, No. 24, Nov. 16, 2010, pp. 18771-18775.

Cong et al., "Implantable Blood Pressure Monitoring of Small Animal for Advanced Biological Research", The 13th International Conference on Solid-State Sensors, Actuators and Microsystems, 2005, Digest of Technical Papers, Transducers '05, IEEE, vol. 2, Jun. 5-9, 2005, pp. 2002-2006.

Cong et al., "Wireless Implantable Blood Pressure Sensing Microsystem Design for Monitoring of Small Laboratory Animals", Sensors and Materials, vol. 20, No. 7, 2008, pp. 327-340.

(56) References Cited

OTHER PUBLICATIONS

EP16773748.5 , "Extended European Search Report", dated Nov. 23, 2018, 7 pages.
EP18798545.2 , "Extended European Search Report", dated Dec. 9, 2020, 5 pages.
Hogg , "Development and Characterisation of Ultrathin Layer Packaging for Implantable Medical Devices", PhD Thesis, University of Applied Sciences, Sep. 5, 2014, 219 pages.
PCT/US2016/023454 , "International Preliminary Report on Patentability", dated Oct. 12, 2017, 15 pages.
PCT/US2016/023454 , "International Search Report and Written Opinion", dated Jun. 27, 2016, 17 pages.
PCT/US2018/026705 , "International Preliminary Report on Patentability", dated Nov. 21, 2019, 7 pages.
PCT/US2018/026705 , "International Search Report and Written Opinion Received", dated Jun. 18, 2018, 8 pages.
Shapero et al., "Parylene-Oil-Encapsulated Low-Drift Implantable Pressure Sensors", 31st IEEE International Conference on Micro Electro Mechanical Systems, Jan. 21-25, 2018, pp. 47-50.
Wheeler et al., "MEMS-Based Bubble Pressure Sensor for Prosthetic Socket Interface Pressure Measurement", Annual International Conference of the IEEE Engineering in Medicine and Biology Society, Aug. 2011, pp. 2925-2928.
Abstract of Shellock FG, Knebel J, Prat AD. Evaluation of MRI issues for a new neurological implant, the Sensor Reservoir. Magn Reson Imaging. Sep. 2013;31(7):1245-50. doi: 10.1016/j.mri.2013.03.012. Epub Apr. 18, 2013. PMID: 23602731.†

\* cited by examiner
† cited by third party

IMPLANTABLE INTRACRANIAL PRESSURE SENSOR

CROSS-REFERENCES TO RELATED APPLICATIONS

This application claims the benefit of U.S. Provisional Application No. 62/962,418, filed Jan. 17, 2020, which is hereby incorporated by reference in its entirety for all purposes.

STATEMENT AS TO RIGHTS TO INVENTIONS MADE UNDER FEDERALLY SPONSORED RESEARCH AND DEVELOPMENT

Not Applicable

BACKGROUND

1. Field of the Art

Embodiments of the present invention generally relate to sensing of intracranial pressure of a patient, including employing one or more electronic sensors within an implantable hydrocephalus shunt for monitoring pressure.

2. Description of the Related Art

Hydrocephalus is a common neurological disease characterized by accumulation of cerebrospinal fluid (CSF) in the brain, usually due to blockage of drainage pathways. This can lead to increased intracranial pressure (ICP) as well as neurologic and cognitive deficits. Hydrocephalus can occur due to various etiologies, such as tumor formation, infection, and trauma, in both neonates and adults. Brain stroke can also cause hydrocephalus.

The current standard treatment for hydrocephalus is the surgical placement of a shunt catheter that drains the CSF from its source in the cerebral ventricles into other body cavities, such as the abdomen or atrium of the heart. The placement of a ventriculoperitoneal shunt (VPS), which diverts CSF from one or more of the brain's ventricles to the peritoneum for absorption, is the most common procedure for hydrocephalus. Other hydrocephalus shunts are employed depending upon the situation. Hydrocephalus shunts are commonly named in light of the intended placement of their inlets and outlets. For example, a ventriculoatrial shunt empties into the heart's atrium, and a lumboperitoneal shunt inputs from the lumber spinal canal (intrathecal).

Over the lifespan of ventriculoperitoneal shunt systems, which can be years, most fail at least once. The main reason for shunt failure is obstruction, with 60% occurring at the proximal (inlet) catheter, 30% at the valve, and the remainder distally (at the output). Noninvasive imaging can suggest shunt failure; however, confirmation involves invasive methods. Those invasive methods involve physically accessing the shunt to measure pressure, flow, and obtain CSF for laboratory and microbiology analysis. The invasive methods also include shunt taps and nuclear medicine shunt studies, as well as surgical intervention to take multiple pressure measurements along the shunt system. These all significantly risk introducing infection into an otherwise sterile environment.

Given the high rates of shunt failure over time and the risks associated with invasive diagnostic methods, there is a need in the art for noninvasive diagnostic methods for assessing hydrocephalus shunts.

BRIEF SUMMARY

A hydrocephalus shunt is outfitted with a biocompatible, long-lasting wireless pressure sensor. The wireless pressure sensor can be mounted within the hollow portion of a hydrocephalus shunt's reservoir, perched in the center on supports or the side so that it does not restrict flow. The wireless pressure sensor can also be mounted in an inline housing anywhere along the shunt's ventricular or distal catheter, and multiple such inline wireless pressure sensors can be deployed depending on a physician's need for monitoring.

To provide long term protection against biofouling, the pressure sensor can have an oil chamber encapsulating its pressure sensitive membrane, the oil chamber having an extremely thin and pliable side composed of a biocompatible polymer such as parylene. The pliable side is positioned in the shunt so that it is protected from needle pricks and other damage by facing it down, protected by other micro-components.

The wireless pressure sensor may have no battery and instead be powered purely through the reception of radio frequency (RF) energy. The RF energy is harvested through a coil antenna connected with a wireless power receiver that converts it immediately into electricity. A reader, which can be mounted in a pillow, cap, handheld instrument, or other item, can send both RF energy for power as well as an ambient, atmospheric pressure measurement of the surrounding air to the implanted wireless pressure sensor. The atmospheric pressure can be used inside the device with the measured pressure of the CSF and temperature to determine a calibrated gauge pressure.

Some embodiments of the present invention are related to a hydrocephalus shunt pressure sensing apparatus including a ventricular catheter, a distal catheter, a reservoir connecting the ventricular catheter and the distal catheter to form a hydrocephalus shunt, a wireless sensor device affixed to the hydrocephalus shunt, the wireless sensor device comprising an electronic pressure sensor, a microprocessor or other digital circuit connected with the electronic pressure sensor, a wireless data transmitter connected with the microprocessor, and an antenna connected with the wireless data transmitter.

The wireless sensor device can be disposed within the reservoir. The reservoir can be comprised of a hollow body mated with a polymer cap, a pressure sensitive membrane of the electronic pressure sensor facing toward the hollow body, and the antenna can be stacked on top of the electronic pressure sensor and face toward the polymer cap. The hollow body can include a rigid frustum, and the polymer cap can be comprised of a resilient silicone. Support posts can project radially from the wireless sensor device to an internal circumference of the reservoir. The wireless sensor device can be centered within the reservoir by the support posts, free and clear within the surrounding cavity.

The apparatus can include an inline sensor housing comprising connectors connected in line with the ventricular catheter or the distal catheter, and an enlarged housing portion surrounding the wireless sensor device. The inline sensor housing can be connected proximal to the reservoir on the ventricular catheter, between a valve and a reservoir, or distal to the valve on the distal catheter.

The electronic pressure sensor can have a pressure sensitive membrane, the wireless sensor device further including an oil chamber encapsulating the pressure sensitive membrane, the oil chamber filled with a biocompatible oil and having a pliable membrane on at least one side. A rigid cage can be arrayed over the pliable membrane.

The wireless sensor device can further include a wireless power receiver connected with the microprocessor, wherein the wireless power receiver is configured to convert radio frequency (RF) energy into instantaneous electricity for the electronic pressure sensor, the microprocessor, and the wireless data transmitter, wherein the instantaneous electricity causes the electronic pressure sensor, the microprocessor, and the wireless data transmitter to take a pressure measurement and transmit a value based on the pressure measurement. A reader can be embedded within a pillow or a wearable cap configured to direct RF energy compatible with powering the wireless power receiver into a subject in which the hydrocephalus shunt pressure sensing apparatus is implanted.

The wireless sensor device can further include a temperature sensor connected with the microprocessor, wherein the microprocessor is configured to compensate pressure measurements based on input from the temperature sensor. A valve can be connected with the ventricular catheter or the distal catheter, and a command wire can be connecting the microprocessor to the valve.

A common housing can surround the electronic pressure sensor, the microprocessor, and the wireless data transmitter. The hydrocephalus shunt pressure sensing apparatus can contain no more than 1 gram of ferromagnetic material and no more than 5 grams of metal, thereby allowing compatibility with a magnetic resonance imaging (MRI) scanner. The ventricular catheter can be suitable as a ventricular or a lumboperitoneal catheter, and the distal catheter can be suitable as a peritoneal catheter or a ventriculoatrial catheter.

Some embodiments are related to a method of manufacturing a hydrocephalus shunt pressure sensor. The method can include providing an electronic pressure sensor, connecting a microprocessor or other digital circuit to the electronic pressure sensor, connecting a wireless data transmitter to the microprocessor, and connecting an antenna to the wireless data transmitter to form a wireless sensor device, and affixing the wireless sensor device to a hydrocephalus shunt having a ventricular catheter, a distal catheter, and a reservoir configured to connect the ventricular catheter and the distal catheter.

The method can include inserting the wireless sensor device into the reservoir. The wireless sensor device can be oriented into a hollow body of the reservoir such that a pressure sensitive membrane of the electronic pressure sensor faces into the hollow body, and the antenna faces outward before mating a polymer cap of the reservoir to the hollow body. The hollow body can include a rigid frustum, and the polymer cap is comprised of a resilient silicone. The method can include attaching support posts to the wireless sensor device before inserting into the reservoir.

The method can include inserting the wireless sensor device into an inline sensor housing and connecting connectors of the inline sensor housing in line with the ventricular catheter or the distal catheter. The inline sensor can be connected proximal to the reservoir on the ventricular catheter, between a valve and a reservoir, or distal to the valve on the distal catheter.

The electronic pressure sensor can have a pressure sensitive membrane, the wireless sensor device further comprising an oil chamber encapsulating the pressure sensitive membrane, the oil chamber filled with a biocompatible oil and having a pliable membrane on at least one side. A rigid cage can be arrayed over the pliable membrane for physical protection.

The method can include connecting a wireless power receiver to the microprocessor, wherein the wireless power receiver is configured to convert radio frequency (RF) energy into instantaneous electricity for the electronic pressure sensor, the microprocessor, and the wireless data transmitter, wherein the instantaneous electricity causes the electronic pressure sensor, the microprocessor, and the wireless data transmitter to take a pressure measurement and transmit a value based on the pressure measurement.

The method can include connecting a temperature sensor with the microprocessor, wherein the microprocessor is configured to compensate pressure measurements based on input from the temperature sensor. The wireless sensor device can be a first wireless sensor device, and the temperature sensor can be a first temperature sensor. The method can further include affixing a second wireless sensor device with a second temperature sensor to a different location on the hydrocephalus shunt, wherein the first and second wireless sensor devices and temperature sensors can give independent measurements of pressure and sensor at their respective locations along the hydrocephalus shunt.

The method can further include connecting a valve in line with the ventricular catheter or the distal catheter and connecting a command wire between the microprocessor to the valve. The method can include surrounding the electronic pressure sensor, the microprocessor, and the wireless data transmitter with a common housing.

Some embodiments related to a method of reading an implanted hydrocephalus shunt pressure sensor, the method including placing a reader onto a subject's head, the subject having implanted therein a hydrocephalus shunt with a wireless sensor device comprising an electronic pressure sensor, a microprocessor or other digital circuit connected with the electronic pressure sensor, a wireless data transmitter connected with the microprocessor, and an antenna connected with the wireless data transmitter, directing power radio frequency (RF) energy toward the wireless sensor device, converting the RF energy to electricity for the electronic pressure sensor, the microprocessor, and the wireless data transmitter, wherein the electricity causes the electronic pressure sensor, the microprocessor, and the wireless data transmitter to take a pressure measurement and transmit a value based on the pressure measurement, and automatically powering down the electronic pressure sensor, the microprocessor, and the wireless data transmitter by halting the RF energy to the wireless sensor device.

The method can include temporarily powering, with the RF energy, a temperature sensor within the wireless pressure sensor device to take a temperature reading, and calculating, in the microprocessor, the value based on the temperature reading. It can also include transmitting, from the wireless data transmitter, the temperature reading as a second value.

The method can include receiving the transmitted value at the reader, measuring an atmospheric pressure with the reader, calculating a gauge pressure based on the transmitted value and atmospheric pressure, and displaying the gauge pressure.

The method can include measuring an atmospheric pressure with the reader, transmitting a signal representing the atmospheric pressure to the wireless sensor device where the microprocessor calculates a gauge pressure based on the signal representing the atmospheric pressure and the pressure measurement, wherein the value based on the pressure measurement includes the gauge pressure.

The method can include receiving the transmitted measurement value on a smart phone and displaying the measurement value on the smart phone. The reader can be integrated into a pillow, and the placing can be accomplished by resting the subject's head on the pillow. The reader can be integrated into a wearable cap, and the placing can be accomplished by the subject donning the cap.

DETAILED DESCRIPTION

An implantation system for long-term intracranial pressure monitoring and recording is presented. A version of the pressure sensor can fit inside a hydrocephalus drainage shunt, and the miniaturized dimensions of the sensor prevents obstruction of the shunt lumen.

In a ventricular catheter of a hydrocephalus shunt, the proximal end of the ventricular shunt is in direct contact with the brain's ventricles. The proximally located sensor allows for the direct measurement of the patient's intracranial pressure (ICP). If the proximal end of the shunt becomes blocked, the sensor will detect lower than normal ventricle pressure indicating proximal ventricle occlusion. If the distal end of the shunt becomes occluded, shunt pressure as measured by the sensor will increase indicating distal shunt occlusion.

A "ventricular catheter" includes catheters that extend into a cerebral ventricle as well as catheters that extend to the lumbar spinal canal (intrathecal), or as otherwise known in the art. A "ventricular catheter" is also known as a "proximal catheter."

A "microprocessor" includes any type of miniature electronic device with arithmetic, logic, and/or control circuitry for performing central processing, or a general or specialized digital circuit that performs translation or reconveying of digital signals using logic or other components, or as otherwise known in the art.

"Instantaneous electricity" from RF energy includes electricity that is immediately and instantaneously converted from RF energy without buffering through chemical batteries or other long-term storage means, or as otherwise known in the art.

A wireless "reader" includes a device that can provoke a wireless sensor device to transmit a pressure measurement or other reading, or as otherwise known in the art. The device can do that by sending power through RF electromagnetic radiation waves to a wireless sensor device in order to power it for measurements and transmission, or it can simply send an interrogation message. As used herein, the term "reader" does not require that any value transmitted from the wireless sensor be received or read by the reader. For example, a reader may trigger the wireless sensor device to transmit, and the transmission may be received and decoded by a smart phone or other electronic device for recording or display.

Sensor locations may include local pressure measurements or distal pressure measurements through the use of a pressure-transducing pigtail catheter that can be attached to the sensor. Integration of the pressure sensor can be introduced within the shunt antecedent to, subsequent to, or at the time of surgery, without any modification to the shunt itself. For example, the pressure sensor can be placed within the reservoir of the shunt.

The pressure sensor can be packaged using the techniques described in U.S. Patent Application Publication No. US 2016/0287101 A1, titled "Biocompatible Packaging for Long Term Implantable Sensors and Electronics." Through this packaging process, the lifespan of biomedical devices can be prolonged through the use of biocompatible materials and minimization of foreign body reaction to the device. Thus, the sensor may be fully implantable within another medical device, such as a shunt, or within the body directly with minimal impact. The pressure sensor may be implanted directly virtually anywhere within the cranium to measure ICP. For example, in cases of traumatic brain injury where patients undergo craniotomy for hematoma drainage, the sensor may be placed below the dura for continuous monitoring of the patient's intracranial pressure.

There are envisioned several interfaces for the integration of the pressure sensor with the hydrocephalus shunts. The sensor can be placed within the proximal metal or rigid plastic connector piece of the shunt that interfaces with the proximal catheter that goes into a patient's ventricle. This sensor is located within the proximal shunt continuum with no modifications of the shunt itself and is charged wirelessly at a predetermined frequency.

The sensor also can include a wireless data transceiver, power receiver, a rechargeable or nonrechargeable battery, and an application specific integrated circuit (ASIC) chip that manages power and data. The device may also contain external passive components like resistors and capacitors, and a memory chip such as an electronically erasable programmable read-only memory (EEPROM). The ASIC chip may be programmable to accommodate rate of sampling, times when to sample, such as only during the day, or 24 hours a day. The ASIC chip can be programmable to change its behavior depending on multiple factors, including rate of change of measurement, time since last measurement, time since last stored measurement, time of day and battery life remaining, and user/doctor input.

The system may uplink data from its data bank to a data repository on a server, through communicating through a personal electronic device, or an application on smartphones. The data may be time-stamped. The records for each patient can be stored cumulatively and can be updated routinely and accessed by doctors without seeing the patient. The device can be powered by other methods, and any or some combination of the following: photovoltaic cells, radiofrequency (near field inductive coupling, mid-field, or far-field) using an on-chip or off-chip antenna, a battery, electrostatic induction by either keeping fixed voltage or fixed charge, capacitive charge transfer for energy storing, optical power transfer, an ultrasonic energy harvester such as transduction by micro-electromechanical system (MEMS) cantilevers or PIT, energy harvested from other vibrations generated by the body, energy from ambient temperature gradients or infrared radiation, electrochemical or fuel cell based energy harvesting.

In the case of inductive coupling, power may be provided by a coil outside. In addition, the energy harvesting could also be achieved by employing metamaterials. The outside coil may reside on something worn, like a mask, for sleeping or as an attachment to glasses, or may be held or fixed to recharge for a period of time. The coil may be integrated into a pillow or device which charges the implant when the patient is laying on a bed.

Several of the features of the device may be including as separate chips or on one or more integrated chips in any combination, such as on-chip capacitors and supercapacitors for energy-storage in complementary metal oxide semiconductor (CMOS) processing.

Figure 1:
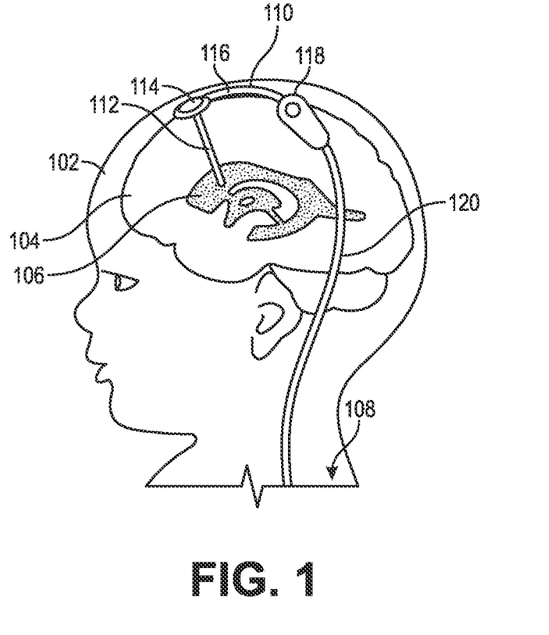
FIG. 1 illustrates a cross section of a subject in which a hydrocephalus shunt is placed in accordance with an embodiment.

FIG. 1 illustrates a cross section of a subject in which a hydrocephalus shunt is placed in vivo in accordance with an embodiment. In subject 102 is brain 104 with ventricle 106. Ventricle 106 is accumulating excess cerebrospinal fluid (CSF), a harbinger of hydrocephalus.

The hydrocephalus shunt shown is generally referred to as a ventriculoperitoneal (VPS) or ventriculoatrial shunt (VAS) because the proximal catheter is placed within the brain's ventricle. As per the definition above, and as a matter of convenience, we refer to a proximal catheter as a ventricular catheter whether it begins in the ventricle, lumbar spinal canal (intrathecal), or other portion of the brain. For example, a proximal catheter in a lumboperitoneal shunt is simply referred to here as a ventricular catheter.

In the figure, whether the end of the distal catheter terminates in the peritoneum 108 or atrium of the heart determines whether the shunt is called a VPS or VAS, respectively. We refer herein to the distal catheter simply as a distal catheter.

Hydrocephalus shunt 110 includes three main parts: ventricular catheter 112, reservoir 114, and distal catheter 120. On distal catheter 120 is one-way valve 118. As shown, section 116 of distal catheter 120 is between valve 118 and reservoir 114.

Figure 2:
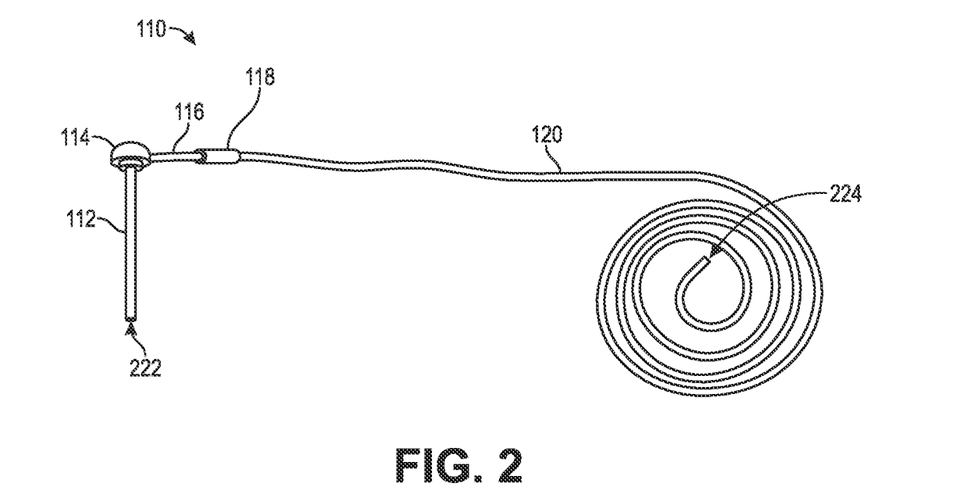
FIG. 2 illustrates a hydrocephalus shunt in vitro in accordance with an embodiment.

FIG. 2 illustrates hydrocephalus shunt 110 before implantation. It is designed such that CSF would enter inlet 222 to ventricular catheter 112 and flow to reservoir 114. The CSF then flows out of reservoir 114 through section 116, one-way valve 118, and the rest of distal catheter 120. It outputs at outlet 224 of distal catheter 120. As common practice in surgical cases, the hydrocephalus shunt pieces come in separate packages that are assembled together to create a functioning hydrocephalus shunt.

Figure 3:
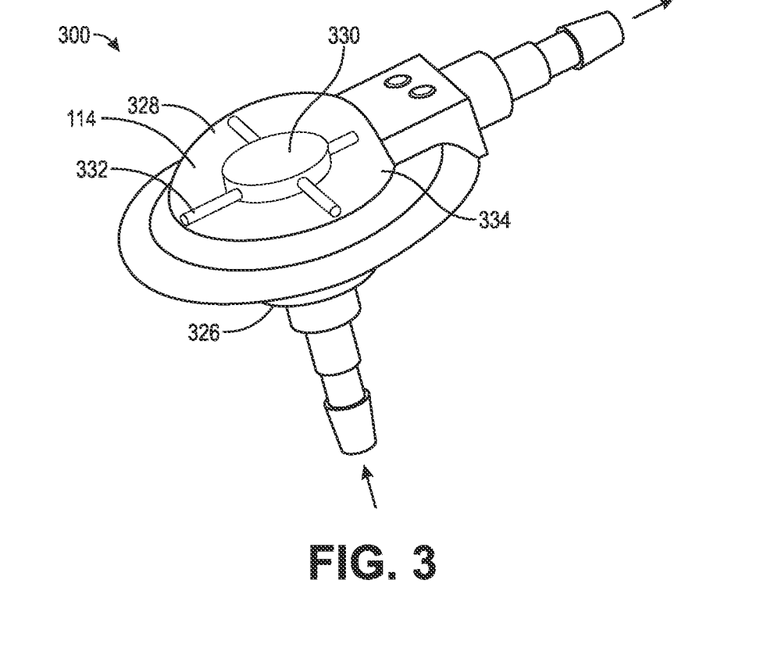
FIG. 3 is a perspective view of a hydrocephalus shunt reservoir with a wireless sensor device shown inside in accordance with an embodiment.

FIG. 3 is a perspective view of a hydrocephalus shunt reservoir housing a wireless sensor device inside in system 300. Reservoir 114 includes hollow body 326 and flexible polymer cap 328 made of a resilient silicone.

Within reservoir 114 is wireless sensor device 330. It is centered within the flow path by support posts 332 that extend radially from wireless sensor device 330 to internal circumference 334 of reservoir 114. The support posts are narrow to allow flow of intracranial fluid around it without any noticeable difference, as the width of the proximal and distal tubes of the hydrocephalus shunt is narrower.

In the exemplary embodiment, support posts lodge the sensor in a fixed position inside the assemblage without an adhesive. Lateral rotation, by external movement, vibration, or fluid flow, will presumably not disturb measurement or wireless power transfer. When placed, the supporting architecture of the sensor will allow for patency of the shunt lumen and prevent movement of the sensor. The static nature of the sensor within the shunt can reduce complications by limiting the motion and the possibility of shunt blockage. Fixed or flexible support posts bound to the sensor may be enough to prevent movement. These support posts may be part of the sensor interface itself or exist as separate structures that are either biocompatible or encapsulated in such a way to allow biocompatibility.

Figure 4:
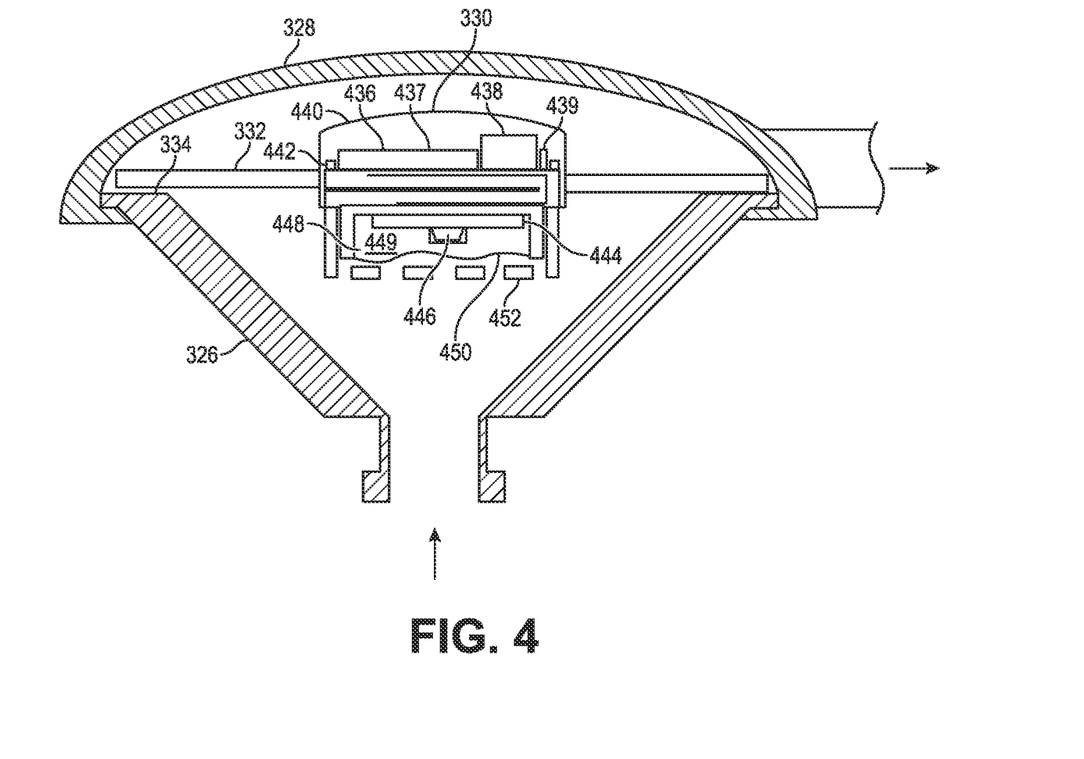
FIG. 4 is a cross section of the hydrocephalus shunt reservoir housing the wireless sensor device of FIG. 3.

FIG. 4 is a cross section of the hydrocephalus shunt reservoir housing the wireless sensor device of FIG. 3. Hollow body 326 is rigid and frustum-shaped with its large end forming circumference 334. On circumference 334 rest support posts 332, held down by an inner surface of polymer cap 328.

Wireless sensor device 330 includes four types of components encapsulated by common housing 440: microprocessor 436, discrete capacitors and resistors, antenna 442, and parylene-on-oil packaged pressure sensor 444. All these components are integrated onto a flexible printed circuit board made of parylene, a USP class VI biocompatible material.

Microprocessor 436, with built-in wireless data transmitter 437, shares the top of the circuit board with components for wireless power receiver 438 and temperature sensor 439. Readings from temperature sensor 439 can be employed to compensate for pressure reading errors that are due to temperature deviations from calibration temperatures. Positioned around the top components is ring antenna 442, which has an unobstructed view up and toward the outside at its nominal 13.56-MHz high frequency (HF).

Additional sensing components can be added to the wireless sensor device, such as flow, vibration, or acceleration sensors, or gyroscopes.

The exemplary wireless sensor device is battery-less. Technical advantages of being battery-less include saving volume, minimizing corrosive battery components, and longevity. To ensure proper function, the external antenna is designed to simultaneously supply a 13.56-MHz H-field power and receive the data. It has been demonstrated that a 20 dBm (100 mW) output power can achieve a 2 cm range from reader to implant with adequate alignment.

Electronic pressure sensor 444 includes a commercial pressure sensing integrated circuit (IC) with a pressure sensitive membrane 446 made of silicon. Oil chamber 448 encapsulates pressure sensitive membrane 446 with biocompatible oil 449 and pliable membrane 450 on the bottom side. Rigid cage 452 is arrayed over pliable membrane 450 to protect it during handling and implantation.

As can be seen from the figure, the pressure sensing side of wireless sensor device 330 faces down into hollow body 326. Meanwhile, antenna 442 is stacked on top and faces upward toward the polymer cap. Technical advantages of this compact design are that it is compatible with existing hydrocephalus shunts and their surgical implementation. The wireless sensor device can even be retrofitted to an existing hydrocephalus shunt already implanted in a patient. The antenna faces toward the outside of the cranium and thus is better accessible to readers that power and/or receive data. The delicate pressure membrane is face down, protected against needles or other instruments that may be used in servicing the shunt.

Besides mounting in a reservoir, the wireless pressure sensor can be employed in inline or pigtail designs.

Figure 5:
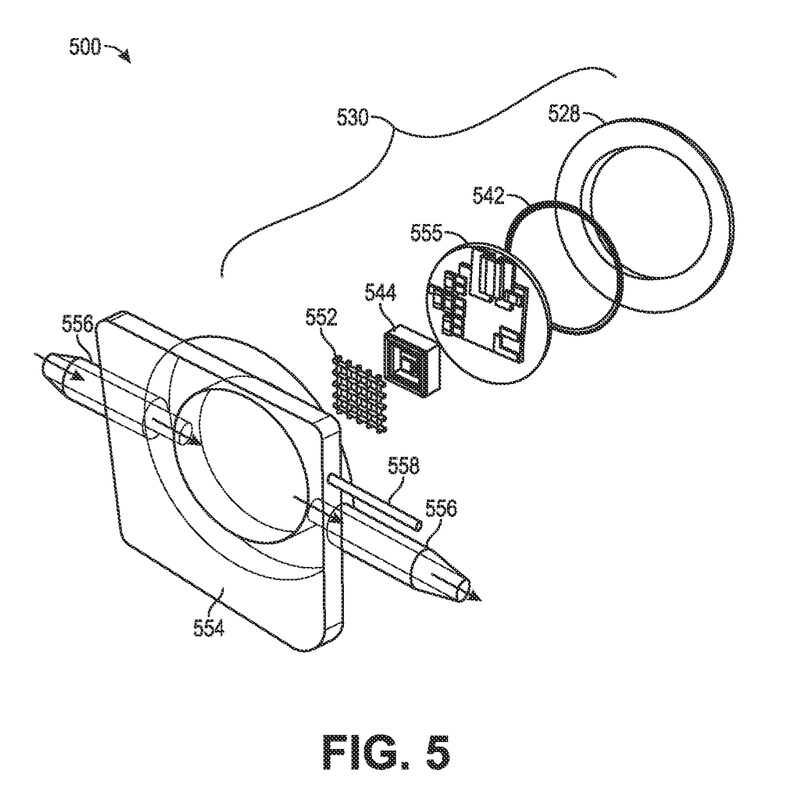
FIG. 5 is an exploded view of an inline wireless sensor device in accordance with an embodiment.
Figure 6:
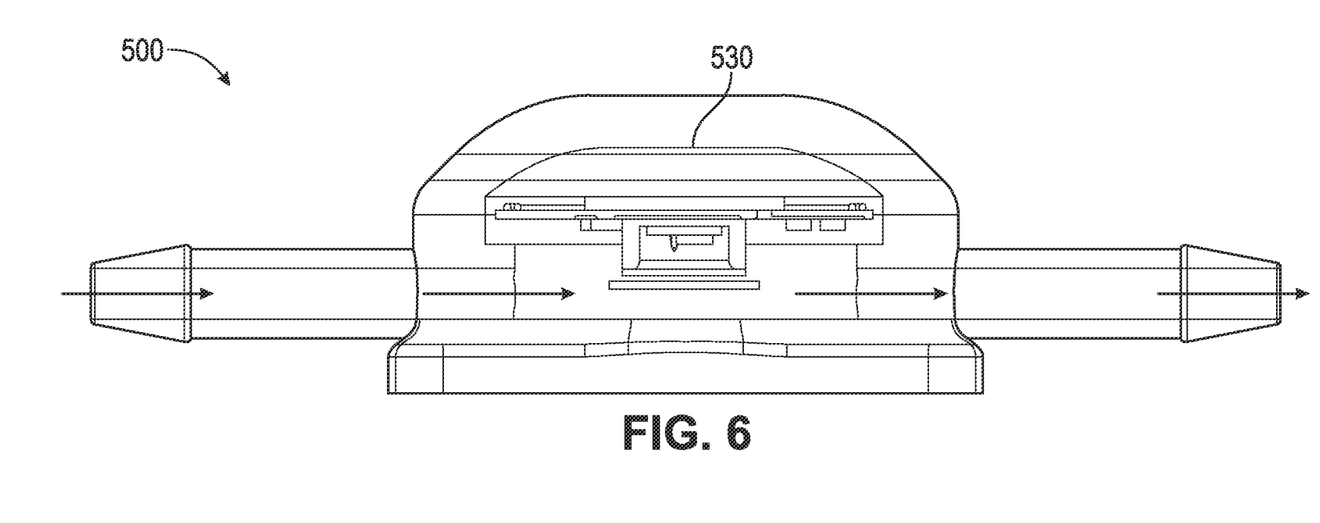
FIG. 6 is a cross section of the inline wireless sensor device of FIG. 5.

FIGS. 5-6 are an exploded view of inline wireless sensor device 500 and a cross section, respectively. Wireless sensor housing 554 includes barbed connectors 556 that are configured to be connected in line with a catheter. The enlarged portion of the housing encloses wireless sensor device 530 and its components with dome 528. The components are largely the same as those described above for that which fits in a reservoir. Rigid cage 552 protects electronic pressure sensor 544, which is mounted on circuit board 555. Ring antenna 542 encircles the circuit board.

Command wire 558 connects the microprocessor of wireless sensor device 530 with a valve. The microprocessor can direct the valve to close or open at small or large intervals. It can also modulate opening the valve in time in order to control CSF flow. This may be controlled wireless by a user or doctor from a reader.

The inline wireless sensor device supports placements of the hydrocephalus shunt in areas other than the reservoir. Over each barbed end of connectors 556 can tightly and hermetically fit a catheter so that pressure can be measured in any fixed location on either of the catheters.

Figure 7:
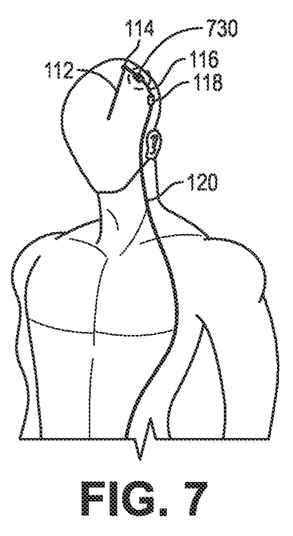
FIG. 7 illustrates a placement of an inline sensor device upstream of a hydrocephalus shunt valve in accordance with an embodiment.
Figure 8:
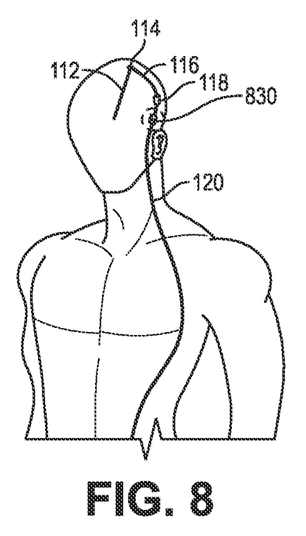
FIG. 8 illustrates a placement of an inline sensor device downstream of a hydrocephalus shunt valve in accordance with an embodiment.
Figure 9:
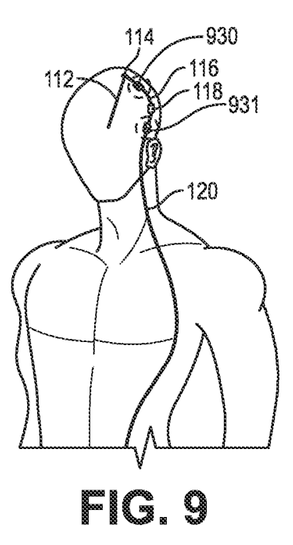
FIG. 9 illustrates a placement of multiple inline sensor devices upstream and downstream of a hydrocephalus shunt valve in accordance with an embodiment.

FIGS. 7-9 illustrate placement of an inline sensor device upstream, downstream, and both upstream and downstream of hydrocephalus shunt valve 118. In FIG. 7, inline pressure sensor device 730 is placed in section 116 of distal catheter 120 between reservoir 114 and valve 118. In FIG. 8, inline pressure sensor device 830 is placed distal to valve 118 on distal catheter 120. In FIG. 9, inline pressure sensor devices 930 and 931 are placed in both locations. If pressure and temperature readings are taken at multiple locations and show, for example, that cooled CSF is not making its way from one measurement point to another, a doctor may assess whether the lumen of a catheter is blocked.

In some embodiments, the pressure sensor device can be place on ventricular catheter 112. Other configurations are envisioned as well. Distal designs allow for further probing of ICP through both direct and indirect methods, which allowing for shunt patency detection, valve diagnostics, ICP measurement, and cerebrospinal fluid flow rate monitoring.

Figure 10:
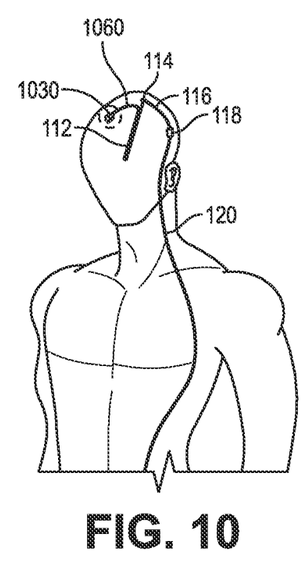
FIG. 10 illustrates a placement of a wireless sensor device off of a shunt from a reservoir of a hydrocephalus shunt valve in accordance with an embodiment.

FIG. 10 illustrates placement of pressure sensor 1030 at the end of a pressure-transducing pigtail catheter 1060 that connects with reservoir 114. The pigtail catheter may also be tapped in order to drain fluid.

The sensor can be magnetic resonance imaging (MRI) safe by limiting its use of ferromagnetic materials to 1 gram with no more than 5 grams of metal total.

Continuous or discrete time measurements may be made through the wireless sensor device. The sensor can be powered by a handheld or other console reader. The reader can power the implant using radio frequency (RF) technology, ultrasound, or other methods, and also retrieve data using those methods such as RF backscattering or ultrasound to receive implant data. If the implant has an energy source such as a battery or photovoltaics, the reader does not need to power the implant.

Figure 11:
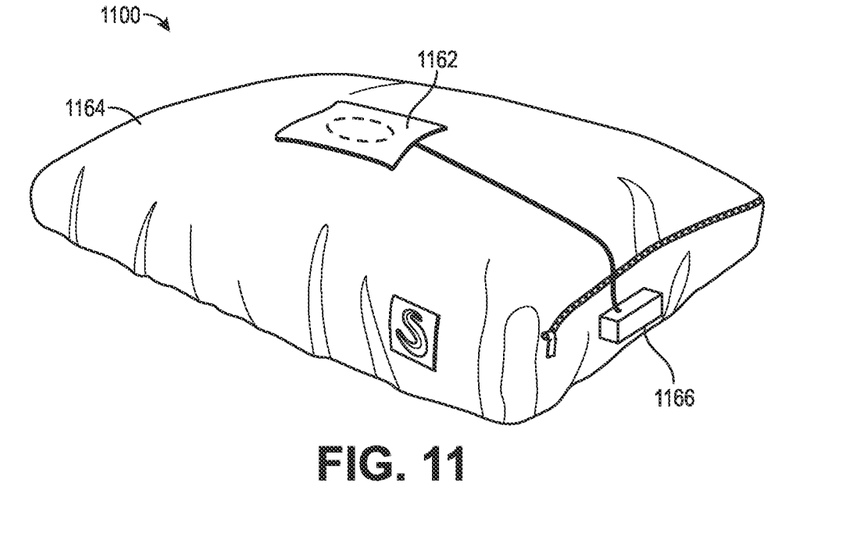
FIG. 11 illustrates a perspective view of a reader embedded within a pillow in accordance with an embodiment.

FIG. 11 illustrates reader system 1100 comprising pillow 1164 and reader 1162. Reader 1162 includes a circular antenna knit into the pillow lining, which can send power to and communicate with an antenna in an implanted wireless sensor device. Control box 1166 houses a transceiver and power element for the antenna as well as an atmospheric pressure measurement transducer. It can measure the ambient, atmospheric pressure and sent it to the implanted sensor so that a gauge pressure can be calculated.

Figure 12:
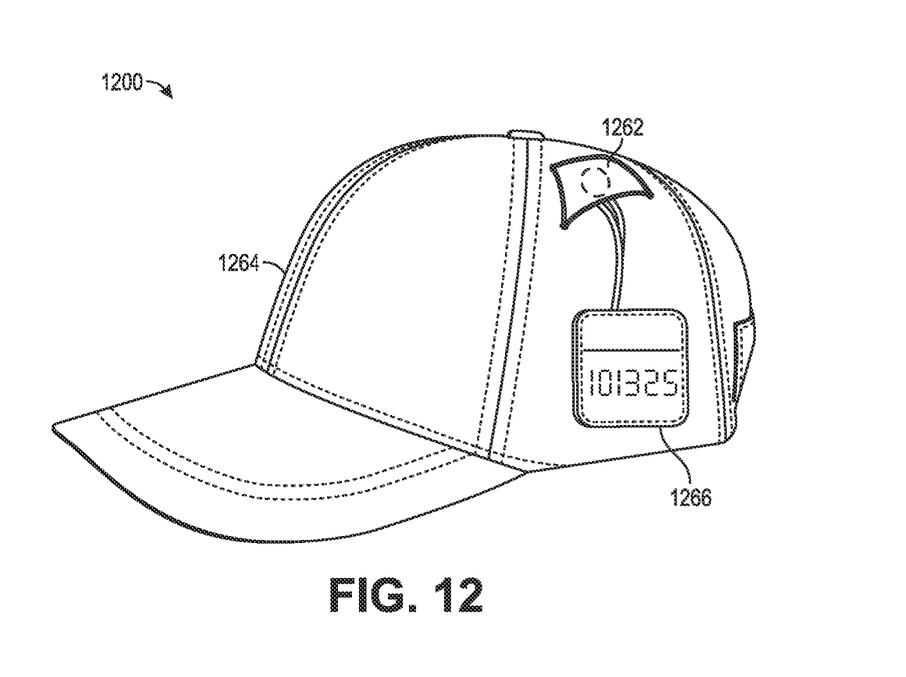
FIG. 12 illustrates a perspective view of a reader mounted on a cap in accordance with an embodiment.

FIG. 12 illustrates reader system 1200 comprising cap 1264 and reader 1262. Reader 1262 includes an antenna mounted in the fabric, which can receive communications from the implanted wireless sensor device. Control box 1266 houses a receiver that receives transmitted pressure and temperature measurements and then displays them instantaneously on a liquid crystal display (LCD).

Figure 13:
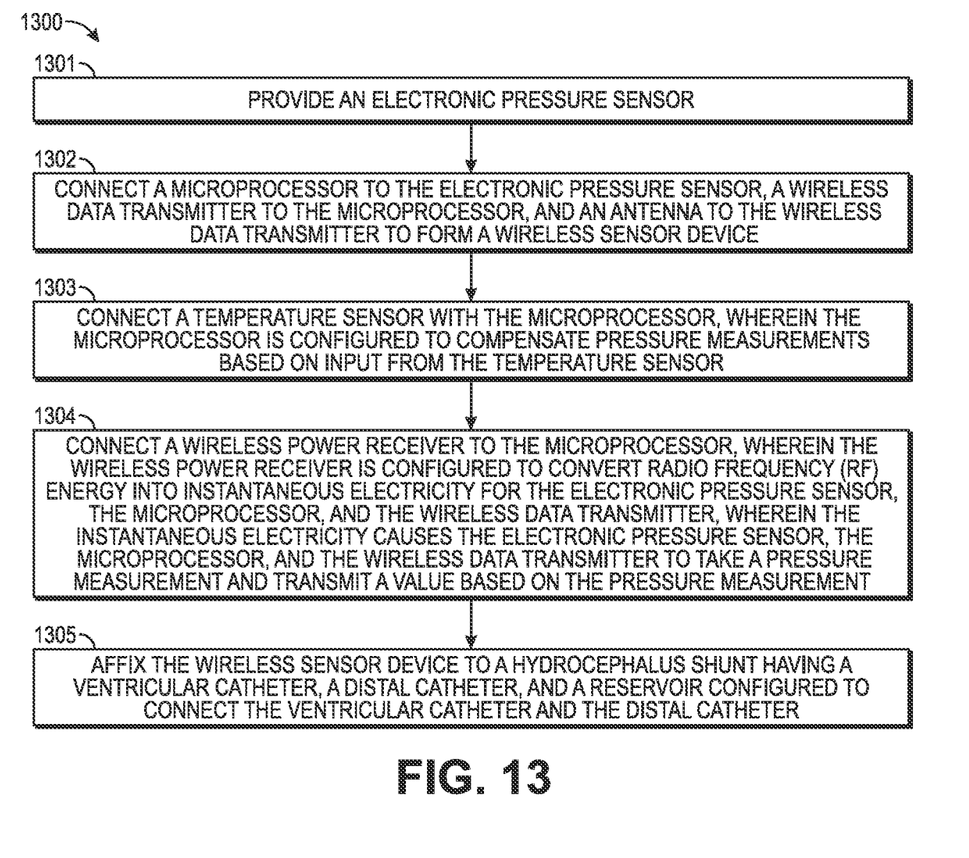
FIG. 13 is a flowchart illustrating a process in accordance with an embodiment.

FIG. 13 is a flowchart illustrating manufacturing process 1300 hydrocephalus shunt pressure sensor in accordance with an embodiment. In operation 1301, an electronic pressure sensor is provided. In operation 1302, a microprocessor or other digital circuit is connected to the electronic pressure sensor, a wireless data transmitter is connected with the microprocessor, and an antenna is connected with the wireless data transmitter, all to form a wireless sensor device. In operation 1303, a temperature sensor is connected with the microprocessor, wherein the microprocessor is configured to compensate pressure measurements based on input from the temperature sensor. In operation 1304, a wireless power receiver is connected to the microprocessor, wherein the wireless power receiver is configured to convert radio frequency (RF) energy into instantaneous electricity for the electronic pressure sensor, the microprocessor, and the wireless data transmitter, wherein the instantaneous electricity causes the electronic pressure sensor, the microprocessor, and the wireless data transmitter to take a pressure measurement and transmit a value based on the pressure measurement. In operation 1305, the wireless sensor is affixed to a hydrocephalus shunt having a ventricular catheter, a distal catheter, and a reservoir configured to connect the ventricular catheter and the distal catheter.

Figure 14:
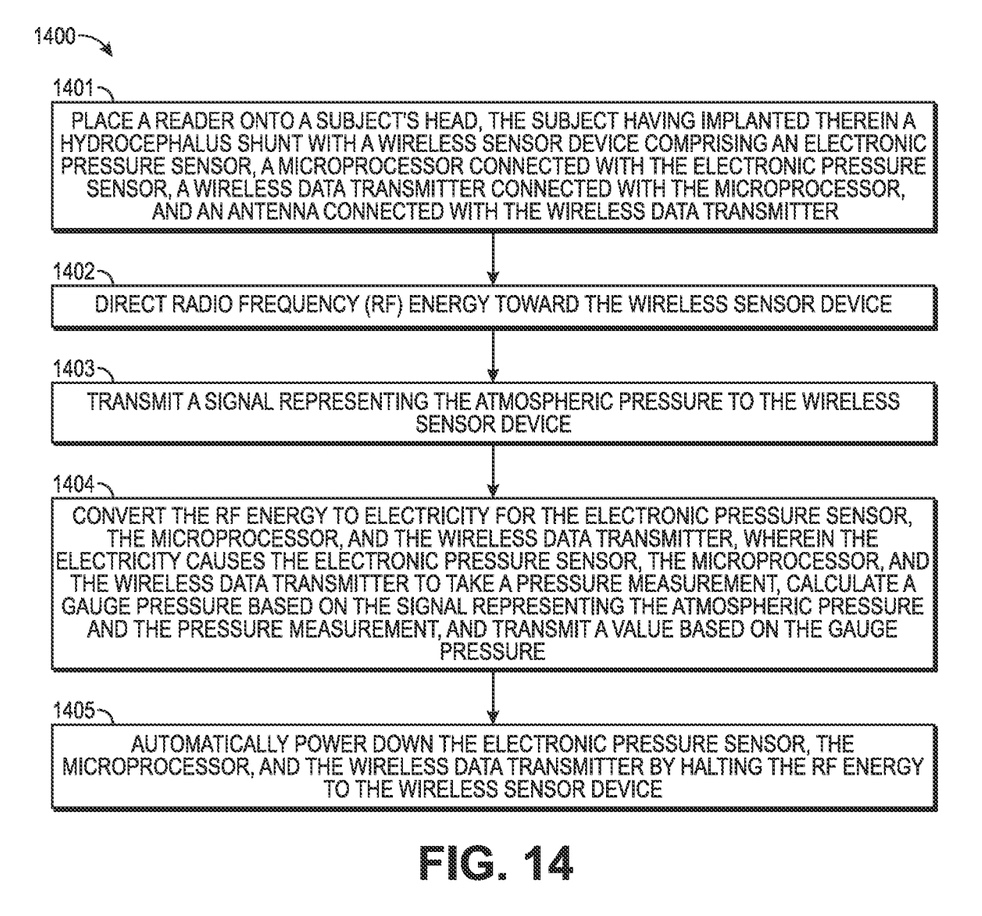
FIG. 14 is a flowchart illustrating a process in accordance with an embodiment.

FIG. 14 is a flowchart illustrating method 1400 of reading a hydrocephalus shunt pressure sensor. In operation 1401, a reader is placed onto a subject's head, the subject having implanted therein a hydrocephalus shunt with a wireless sensor device comprising an electronic pressure sensor, a microprocessor or other digital circuit connected with the electronic pressure sensor, a wireless data transmitter connected with the microprocessor, and an antenna connected with the wireless data transmitter. In operation 1402, radio frequency (RF) energy is directed toward the wireless sensor device. In operation 1403, a signal representing the atmospheric pressure is transmitted to the wireless sensor device. In operation 1404, the RF energy is converted to electricity for the electronic pressure sensor, the microprocessor, and the wireless data transmitter, wherein the electricity causes the electronic pressure sensor, the microprocessor, and the wireless data transmitter to take a pressure measurement, calculate a gauge pressure based on the signal representing the atmospheric pressure and the pressure measurement, and transmit a value based on the gauge pressure. In operation 1405, the electronic pressure sensor, the microprocessor, and the wireless data transmitter are automatically powered down by halting the RF energy to the wireless sensor device.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain. "About" in reference to a temperature or other engineering units includes measurements or settings that are within ±1%, ±2%, ±5%, ±10%, or other tolerances of the specified engineering units as known in the art.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A hydrocephalus shunt pressure sensing apparatus comprising:
    a ventricular catheter;
    a distal catheter;
    a reservoir connecting the ventricular catheter and the distal catheter to form a hydrocephalus shunt;
    a pigtail catheter connected to the ventricular catheter; and
    a wireless sensor device sensing on the ventricular pigtail catheter, the wireless sensor device comprising:
        an electronic pressure sensor;
        a microprocessor connected with the electronic pressure sensor;
        a wireless data transmitter connected with the microprocessor; and
        an antenna connected with the wireless data transmitter.

2. The apparatus of claim 1 wherein the electronic pressure sensor has a pressure sensitive membrane, the wireless sensor device further comprising:
    an oil chamber encapsulating the pressure sensitive membrane, the oil chamber filled with a biocompatible oil and having a pliable membrane on at least one side.

3. The apparatus of claim 2 further comprising:
    a rigid cage arrayed over the pliable membrane.

4. The apparatus of claim 1 wherein the wireless sensor device further comprises:
    a wireless power receiver connected with the microprocessor, wherein the wireless power receiver is configured to convert radio frequency (RF) energy into instantaneous electricity for the electronic pressure sensor, the microprocessor, and the wireless data transmitter,
    wherein the instantaneous electricity causes the electronic pressure sensor, the microprocessor, and the wireless data transmitter to take a pressure measurement and transmit a value based on the pressure measurement.

5. The apparatus of claim 4 further comprising:
    a reader embedded within a pillow or a wearable cap configured to direct RF energy compatible with powering the wireless power receiver into a subject in which the hydrocephalus shunt pressure sensing apparatus is implanted.

6. The apparatus of claim 1 wherein the wireless sensor device further comprises:
    a temperature sensor connected with the microprocessor, wherein the microprocessor is configured to compensate pressure measurements based on input from the temperature sensor.

7. The apparatus of claim 1 further comprising:
    a valve connected with the ventricular catheter or the distal catheter; and
    a command wire connecting the microprocessor to the valve.

8. The apparatus of claim 1 further comprising:
    a common housing surrounding the electronic pressure sensor, the microprocessor, and the wireless data transmitter.

9. The apparatus of claim 1 wherein the hydrocephalus shunt pressure sensing apparatus includes no more than 1 gram of ferromagnetic material and no more than 5 grams of metal, thereby allowing compatibility with a magnetic resonance imaging (MRI) scanner.

10. The apparatus of claim 1 wherein the ventricular catheter is suitable as a ventricular or a lumboperitoneal catheter, and the distal catheter is suitable as a peritoneal catheter or a ventriculoatrial catheter.

11. A method of manufacturing a hydrocephalus shunt pressure sensor, the method comprising:
   providing an electronic pressure sensor;
   connecting a microprocessor to the electronic pressure sensor, a wireless data transmitter to the microprocessor, and an antenna to the wireless data transmitter to form a wireless sensor device;
   affixing the wireless sensor device to a pigtail catheter; and
   connecting the pigtail catheter to a ventricular catheter of a hydrocephalus shunt, the hydrocephalus shunt having the ventricular catheter, a distal catheter, and a reservoir configured to connect the ventricular catheter and the distal catheter.

12. The method of claim 11 wherein the electronic pressure sensor has a pressure sensitive membrane and the wireless sensor device further comprises:
   an oil chamber encapsulating the pressure sensitive membrane, the oil chamber filled with a biocompatible oil and having a pliable membrane on at least one side.

13. The method of claim 11 wherein the wireless sensor device further comprises:
   a temperature sensor connected with the microprocessor, wherein the microprocessor is configured to compensate pressure measurements based on input from the temperature sensor.

14. The method of claim 11 wherein the wireless sensor device further comprises:
   a valve connected with the ventricular catheter or the distal catheter; and
   a command wire connecting the microprocessor to the valve.

15. The method of claim 11 wherein the hydrocephalus shunt pressure sensor includes no more than 1 gram of ferromagnetic material and no more than 5 grams of metal, thereby allowing compatibility with a magnetic resonance imaging (MRI) scanner.

16. A method of reading an implanted hydrocephalus shunt pressure sensor, the method comprising:
   placing a reader onto a subject's head, the subject's head having implanted therein a hydrocephalus shunt with a wireless sensor device affixed to a pigtail catheter, the pigtail catheter connected to a ventricular catheter of the hydrocephalus shunt, the wireless sensor device comprising an electronic pressure sensor, a microprocessor connected with the electronic pressure sensor, a wireless data transmitter connected with the microprocessor, and an antenna connected with the wireless data transmitter;
   directing radio frequency (RF) energy toward the wireless sensor device;
   converting the RF energy to electricity for the electronic pressure sensor, the microprocessor, and the wireless data transmitter, wherein the electricity causes the electronic pressure sensor, the microprocessor, and the wireless data transmitter to take a pressure measurement and transmit a value based on the pressure measurement; and
   automatically powering down the electronic pressure sensor, the microprocessor, and the wireless data transmitter by halting the RF energy to the wireless sensor device.

17. The method of claim 16 wherein the electronic pressure sensor has a pressure sensitive membrane and the wireless sensor device further comprises:
   an oil chamber encapsulating the pressure sensitive membrane, the oil chamber filled with a biocompatible oil and having a pliable membrane on at least one side.

18. The method of claim 16 wherein the wireless sensor device further comprises:
   a temperature sensor connected with the microprocessor, wherein the microprocessor is configured to compensate pressure measurements based on input from the temperature sensor.

19. The method of claim 16 wherein the wireless sensor device further comprises:
   a valve connected with the ventricular catheter or a distal catheter of the hydrocephalus shunt; and
   a command wire connecting the microprocessor to the valve.

20. The method of claim 16 wherein the hydrocephalus shunt pressure sensor includes no more than 1 gram of ferromagnetic material and no more than 5 grams of metal, thereby allowing compatibility with a magnetic resonance imaging (MRI) scanner.

* * * * *